US005614608A

United States Patent [19]
Krchnak et al.

[11] Patent Number: 5,614,608
[45] Date of Patent: Mar. 25, 1997

[54] APPARATUS AND METHOD FOR MULTIPLE SYNTHESIS OF ORGANIC COMPOUNDS ON POLYMER SUPPORT

[75] Inventors: Viktor Krchnak; Michal Lebl; Bruce Seligmann, all of Tucson, Ariz.

[73] Assignee: Selectide Corporation, Del.

[21] Appl. No.: 375,879

[22] Filed: Jan. 20, 1995

[51] Int. Cl.$^6$ ............... B01J 8/02; C07K 1/04; C08F 283/00
[52] U.S. Cl. ............ 530/334; 395/906; 422/116; 525/54.11
[58] Field of Search .................. 395/904, 906; 525/54.1, 54.11; 528/312, 328; 530/334, 810; 422/116; 935/88

[56] References Cited

U.S. PATENT DOCUMENTS

| | | | |
|---|---|---|---|
| 5,147,608 | 9/1992 | Hudson et al. | 530/334 |
| 5,368,823 | 11/1994 | McGraw et al. | 422/116 |

FOREIGN PATENT DOCUMENTS 529504  3/1993  European Pat. Off. .

OTHER PUBLICATIONS

Biochem. Soc. Trans., vol. 20, issued 1992, Fox, "Automatic Multiple peptide synthesis", pp. 851–853.
Tetrahedron, vol. 45, No. 24, issued 1989, Schnorrenberg et al, "Fully Automatic Simultaneous Multiple . . . ", pp. 7759–7764.
Int. J. Peptide Protein Res., vol. 40, issued 1992, Zuckermann et al, "Design, construction and application . . . ", pp. 497–506.

Primary Examiner—Jeffrey E. Russel
Attorney, Agent, or Firm—Pennie & Edmonds

[57] ABSTRACT

A solid phase synthesis system is provided by employing a fully automated robot that operates with a novel timing protocol for handling multiple synthetic tasks efficiently. The novel timing protocol is realized by performing steps in the synthesis cycles for different compounds, such as peptides, concurrently rather than on a sequential basis.

39 Claims, 4 Drawing Sheets

APPARATUS AND METHOD FOR MULTIPLE SYNTHESIS OF ORGANIC COMPOUNDS ON POLYMER SUPPORT

REFERENCE TO MICROFICHE APPENDIX

A microfiche appendix consisting of two (2) microfiches and of a hundred twenty (120) frames is included as a part of the specification. The microfiche appendix contains a program listing implementing the present invention. The program listing is subject to copyright protection. The copyright owner, however, has no objection to the facsimile reproduction by anyone of the program listing, as it appears in the Patent and Trademark Office file or records, but otherwise reserves all copyright rights whatsoever.

TECHNICAL FIELD

This invention relates to an apparatus and method for the multiple synthesis of compounds consisting essentially of repeating structural units formed, for example, by repeated washing, deprotection, and coupling. More particularly, the invention is directed to a system for the multiple synthesis of organic compounds, such as peptides, which uses an automated robot for handling multiple synthetic tasks.

BACKGROUND OF THE INVENTION

Systems for the synthesis of organic compounds, for example peptides, are highly desired for many applications. For example, the synthesis and collection of a large number of peptides would assist in the development of agents that could block, promote or otherwise affect cellular reactions that involve recognition and binding. These agents would be useful in the treatment or diagnosis of a number of diseases. More particularly, synthetic peptides can be used as diagnostic and therapeutic agents.

Understandably, peptide synthesis systems have been designed and constructed. Houghten. R. A., *Proc. Natl Acad. Sci.*, 82: 5131–5135 (1985), employs a "tea bag" method using standard Boc amino acid resin in polypropylene mesh packets with standard washing, deprotection, neutralization, and coupling protocols of the original solid phase procedure of Merrifield, R. B., *J. Amer. Chem Soc.*, 85: 2149–2154 (1963).

Although some peptide synthesis systems have been automated for the synthesis of multiple peptides, they generally exhibit poor "respite" time, unable to handle efficiently multiple synthetic tasks. For example, commercial peptide synthesis systems, such as those from Gilson, U.S.A. and Advanced Chem Tech, are capable of synthesizing multiple peptide sequences. However, these automated synthesis systems perform each step in the synthetic cycles for all peptides one by one or sequentially. The timing protocol, more specifically, involves washing all peptides one by one, deprotecting all peptides one by one and then coupling all peptides one by one. For example, coupling is initiated for a first peptide and then when those first initiation coupling steps are completed, coupling is initiated for a second peptide. Such a timing protocol results in an especially long delay or respite time between peptide synthesis steps. Washing all peptides one by one is time consuming. Moreover, during coupling, the system is idle while waiting for coupling to finish. With coupling taking up to 2 hours, the efficiency of prior art automated synthesis systems is severely limited.

Furthermore, prior art automated peptide synthesis systems critically lack flexibility. Once the synthesis of a peptide set has started, any additional peptides, even those urgently required, cannot be started. Furthermore, prior art systems lack the flexibility so as to execute more than one type of coupling reaction, which is typically required for the synthesis of non-peptide compounds.

SUMMARY OF THE INVENTION

A novel synthesis system overcoming the drawbacks of the prior art is realized by employing a fully automated robot that operates with a novel timing protocol for handling multiple synthetic tasks efficiently. The novel timing protocol is realized by performing different steps in the synthesis cycles for multiple organic compounds concurrently rather than on a sequential basis.

Advantageously, this novel timing protocol provides the flexibility of readily adding desired compounds to the list of compounds to be synthesized, changing the order in which the compounds are synthesized, or deleting previously entered compounds. More importantly, such a timing approach or protocol decreases the "respite" time—new synthesis steps of the next compound synthesis being initiated prior to the completion of those in the previous synthesis.

In an exemplary embodiment, the novel synthesis system includes an industrial robot system operating under computer control for effecting the synthesis steps within each cycle of the selected compounds, for example, peptides. Each synthetic cycle comprises five different steps: washing, adding deprotection reagents, deprotection, adding coupling reagents and coupling. Because deprotection and coupling do not involve any robot action they are passive synthetic steps, although chemically active; the other steps are active synthetic steps.

Importantly, the novel timing protocol is realized by having the robot system, during the passive synthetic steps of a compound synthesis, perform active synthetic steps for the synthesis cycle of the synthesis of the next compound.

In a preferred embodiment of the invention, a solid-phase peptide synthesis is used, with a first set of plastic syringes containing the resin used as the solid support and serving as the reaction vessel. Additionally, a second set of plastic syringes contains amino acids. The robot system equipped with a gripper arm positions any one of the plurality of syringes to selectively aspirate and dispense solvents and reagents from the desired syringe in accordance with the novel timing protocol for coupling predetermined amino acids to the solid support.

BRIEF DESCRIPTION OF THE DRAWINGS

A more complete understanding of the invention may be obtained by reading the following description in conjunction with the appended drawing in which like elements are labeled similarly and in which.

DETAILED DESCRIPTION

The invention relates to an apparatus for the multiple synthesis of compounds consisting essentially of repeating structural units, for example peptides, formed by repeated washing, deprotection, and coupling. The apparatus or synthesis system employs a fully automated robot system that operates with a novel timing protocol for handling multiple synthetic tasks efficiently. The novel timing protocol is realized by performing different steps in the different synthesis cycles of multiple organic compounds concurrently rather than on a sequential basis, as discussed in more detail below.

Without any loss of generality or applicability for the principles of the present invention, the overall operation of the present invention is described using, as an example, Fmoc/tBu chemistry, applied to the Merrifield solid phase synthesis of peptides. It should, however, be understood that the present invention is equally applicable to any other chemistry for the solid phase synthesis of compounds that consist essentially of repeating structural units, such as polymers or organic compounds as described, for example, in Borchardt et al., *J. Am. Chem. Soc.*, 116: 373 (1994); Chen et al., *J. Am. Chem. Soc.*, 116: 2661 (1994); Simon et al., *PNAS*, 89: 9367 (1992); Nikolaiev et al., *Pept. Res.*, 6: 161–70 (1993); and Lebl et al., Vol. 5: 541–548, *Techniques In Protein Chemistry*, Academic Press, San Diego (1994), which are incorporated herein by reference.

Before describing the present invention, however, it will be instructive to discuss briefly the basic principles of peptide synthesis. Peptide synthesis involves the coupling of amino acids and may be accomplished by techniques familiar to those skilled in the art. See, for example, Stewart and Young, *Solid Phase Synthesis*, Second Edition, Pierce Chemical Co., Rockford, Ill. (1984), which is incorporated herein by reference.

The process of peptide synthesis on solid supports generally involves building a peptide from the carboxyl or C-terminal end in which the C-terminal amino acid with its protected α-amino group is attached to a solid phase polymer. The protecting group is then cleaved off, and the next amino acid, also protected, is coupled by a peptide bond to the α-amino group of the amino acid attached to the solid support. The cycle of deprotecting the prior amino acid and coupling the additional amino acid is repeated until the desired peptide is synthesized. Any reactive side chains of the amino acids are protected by chemical groups that can withstand the coupling and Nα-deprotection procedure. These side chain protecting groups, however, can be removed at the end of the synthesis.

In order to couple an amino acid to the growing synthetic chain, the carboxyl group of the blocked amino acid must be activated. Many methods of activation may be used, including, for example, preformed symmetrical anhydrides (PSA), preformed mixed anhydride (PMA), acid chlorides, active esters, and in situ activation of the carboxylic acid.

Figure 1:
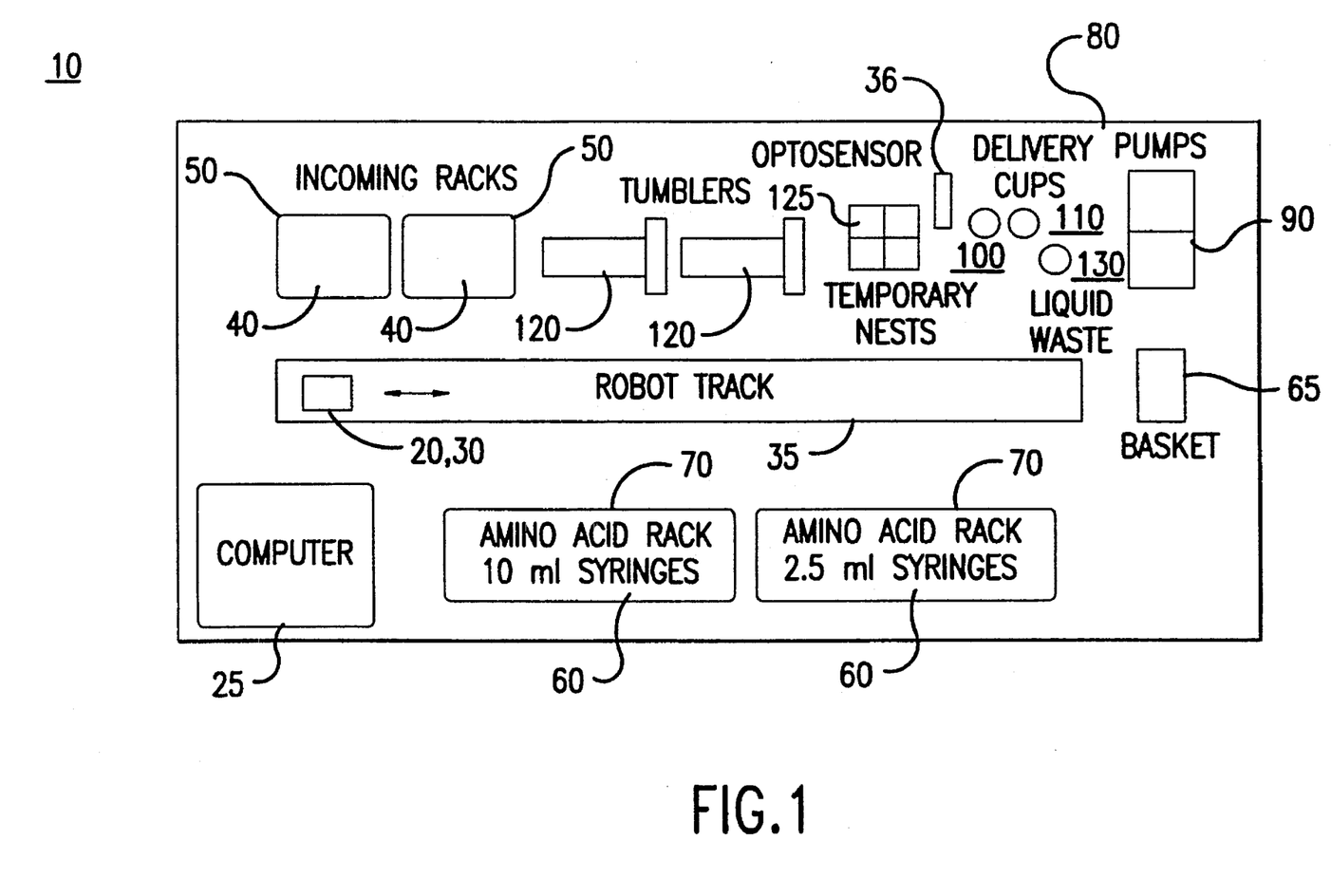
FIG. 1 is a block diagram of a synthesis system in accordance with the principles of the invention.

The present synthesis system includes a fully automated robot system interfaced to a computer for effecting the synthesis cycle of each desired peptide to be synthesized. Referring to FIG. 1, there is illustrated a block diagram of a preferred embodiment of a system for the multiple synthesis of compounds, more particularly peptides, applying standard Fmoc/tBu chemistry in accordance with the principles of the invention.

Synthesis system 10 comprises an industrial robot system 20, such as Model A251 from CRC Plus, Inc., Harrington, Canada, that is interfaced to a IBM personal computer 25. Computer 25 includes such hardware as a central processing unit, program and random access memories, timing and control circuitry, input and output interface devices, and other digital subsystems necessary to the operation of the central processing unit, all of which are well known and understood in the art. Accordingly, such computer hardware is not discussed herein for the sake of clarity.

Robot system 20 is programmed to effect different mechanical manipulations through the use of pre-programmed steps typically provided for in software programs delivered with the robot system. Alternatively, such preprogrammed steps can be provided for in third party software programs, such as Total Control For Windows, Hudson Control Group Inc., Springfield, N.J. Those skilled in the art will readily note that other computer means, microcomputer control means or other automated control means, including other programming software, may be alternatively provided to effect mechanical manipulations.

Automated robot system 20 equipped with a gripper arm 30 that is movable under program control along track 35 can pick up and position (X,Y,Z) any one of a plurality of syringes to any predetermined location. The gripper arm is used to selectively aspirate and dispense solvents and reagents from the desired syringe which serves as the reaction vessel for coupling predetermined amino acids to a solid support. More particularly, each syringe has a plunger that is movable by the gripper arm so as to aspirate or dispense reagents in a manner well known to those skilled in the art. See, for example, Krchnak, V., Vagner, J., "Color-Monitored Solid-Phase Multiple Peptide Synthesis Under Low-Pressure Continuous Flow Conditions," *Peptide Res.* 3, 182 (1990), which is incorporated herein by reference. Moreover, the gripper arm provides a means for shaking the contents of the syringes. Also, the content amount of reagents in each syringe can be readily determined by detecting the position of the plunger within the desired syringe. Also, to confirm that the syringe has been properly gripped and positioned, an optical sensor 36 detecting the motion of the syringes is preferably used to provide feedback to the synthesis system.

A suitable solid support may be selected, such as a polystyrene or polyethylene glycol/polystyrene resin. The protected amino acids may be readily obtained from a number of places, such as Bachem (Torrance, Calif.), Advanced ChemTech (Louisville, Ky.) or Propeptide (Vertle-Petit, France).

Importantly, computer 25 also controls when each step in the synthesis cycle is initiated so as to implement the novel timing protocol of the present invention wherein different steps in the synthesis cycles of multiple peptides are performed concurrently rather than on a sequential basis.

More particularly, synthesis system 10 includes a first set of plastic syringes 40 for holding resin used as the solid support, herein referred to as "resin syringes." In the preferred embodiment, RAM-TentaGel (0.21 mmol/g) obtained from Rapp-Polymere, Tubingen, Germany, is used as the resin.

First set of plastic resin syringes 40 is placed in incoming racks 50, each holding up to, for example, thirty 10 ml and thirty 2.5 ml syringes. Synthesis system 10 also includes a second set of plastic syringes 60 for holding amino acid solutions, herein referred to as "amino acid syringes." Similarly, second set of syringes 60 are placed in racks 70, each holding up to, for example, a hundred 10.0, ml and a hundred 2.5 ml syringes. Basket 65 holds the completed synthesized peptides. The number and size of the first and second sets of syringes will be dependent on the number of different peptides synthesized, the length of the peptides and the number of different amino acids required.

Plastic syringes 40, 60 preferably are made of a material, such as polypropylene, that is sufficiently chemically inert to all solvents and reagents used in the solid-phase peptide synthesis, including trifluoroacetic acid. Alternative materials include Kevlar, Teflon or cast glass.

Each plastic resin syringe 40, which serves as the reaction vessel, is equipped at the bottom with a frit (not shown). It should be understood that various other vessels and means for retaining the solid phase and removing the excess reagents and solvents may be used. For example, columns or wells fitted with a frit or filter may be used as alternative reaction vessels that are compatible with the present synthesis system. In that alternative, the columns or wells are connected to a vacuum source in such a manner that they can be disconnected from the reaction vessel. Moreover, the frit or the means for retaining the solid phase does not have to be integral with the reaction vessel. Rather, it can be external or only present when necessary to retain the solid phase during the removal of solution therefrom.

Appropriate solvents and reagents are introduced from solvent reservoirs to delivery cups 80 using four 10 ml piston pump systems 90, such as the Hamilton MicroLab 900, Reno Nev. Commercial-grade solvents and reagents, such as dimethylformaminde (DMF), piperidine/DMF, DIC/DMF, are used. Three of the piston pumps deliver solvents and reagents to delivery cups 80 whereas the fourth piston pump removes waste as well as wash solution from cups 80 where the amino acids and the coupling reagents are mixed.

Delivery cups 80 comprise a first cup 100 that is used for all washing and for receiving the protected amino acids and coupling reagents, and a second cup 110 that is used for receiving deprotection reagents.

Those skilled in the art will readily note that further independent manipulating stations may be used to manipulate the syringes, depending on the particular reaction desired therein, such as dispensing, aspirating, shaking, heating, cooling or even refluxing. In those instants, robot system 20 would only be required to position the appropriate syringes in the desired manipulating stations. This would decrease the required time to perform the active synthetic steps because the most time consuming tasks would be distributed among multiple and independent manipulating stations.

Using the above synthesis system, multiple peptides are synthesized by manipulating the syringes so as to repeatably attach during a synthetic cycle a desired amino acid to the solid support. Those skilled in the art will note that there is neither a physical link, such as tubing and valves, between the reagent vessels and the reaction vessels nor between the mixing chambers and the reaction vessels. As such, different reagents and reaction conditions may be used within the same or different peptide synthesis.

Each synthetic cycle consists of the following sequence of basic operations or steps: washing, adding deprotection reagents, deprotection, adding coupling reagents, and coupling. Judiciously combining synthetic cycles, each coupling a desired amino acid, creates a synthesis protocol for the synthesis of the desired peptide. Only three of the above synthetic steps, washing, adding deprotection reagents and adding coupling reagents, however, directly require the use of robot system 20. These steps are referred herein to as "active synthetic steps," although chemically passive, and are discussed in more detail below.

During washing, robot system 20 positions a selected resin syringe from rack 40, a tumbler 120 or holding position 125 and then dispenses any liquid therein into liquid waste 130. A preprogrammed amount of washing liquid is subsequently delivered to first cup 100 using piston pump system 90 and then aspirated together with a preprogrammed amount of air using the selected resin syringe. Robot system 20 finally then shakes the selected resin syringe for a preprogrammed time to ensure efficient mixing.

Adding deprotection reagents similarly requires the use of robot system 20. Robot system 20 positions the desired resin syringe over liquid waste 130 and dispenses any liquid therein. A preprogrammed amount of deprotection mixture is subsequently delivered to second cup 110 and then aspirated together with a preprogrammed amount of air using the selected resin syringe.

Lastly, adding coupling reagents also requires the use of robot system 20. Robot system 20 positions the selected resin syringe in holding position 125. Robot system 20 then selects and positions a selected amino acid syringe, dispensing a predetermined amount of desired amino acid into first cup 100. The selected amino acid syringe is repositioned in rack 40. A preprogrammed amount of activating agents is then delivered to first cup 100 and aspirated together with a preprogrammed amount of air using the selected resin syringe located in holding position 125. That selected resin syringe is then positioned into tumbler 120. Next, robot system 20 dispenses a preprogrammed amount of washing solvent into first cup 100 which is then aspirated. Typically, the latter steps of tumbling and washing are repeated a number of times, preferably three times.

During deprotection and coupling, the syringes are placed on 2.5 ml or 10.0 ml tumbling racks 120, each of which holds up to 18 syringes, to ensure an efficient mixing.

Figure 2A:
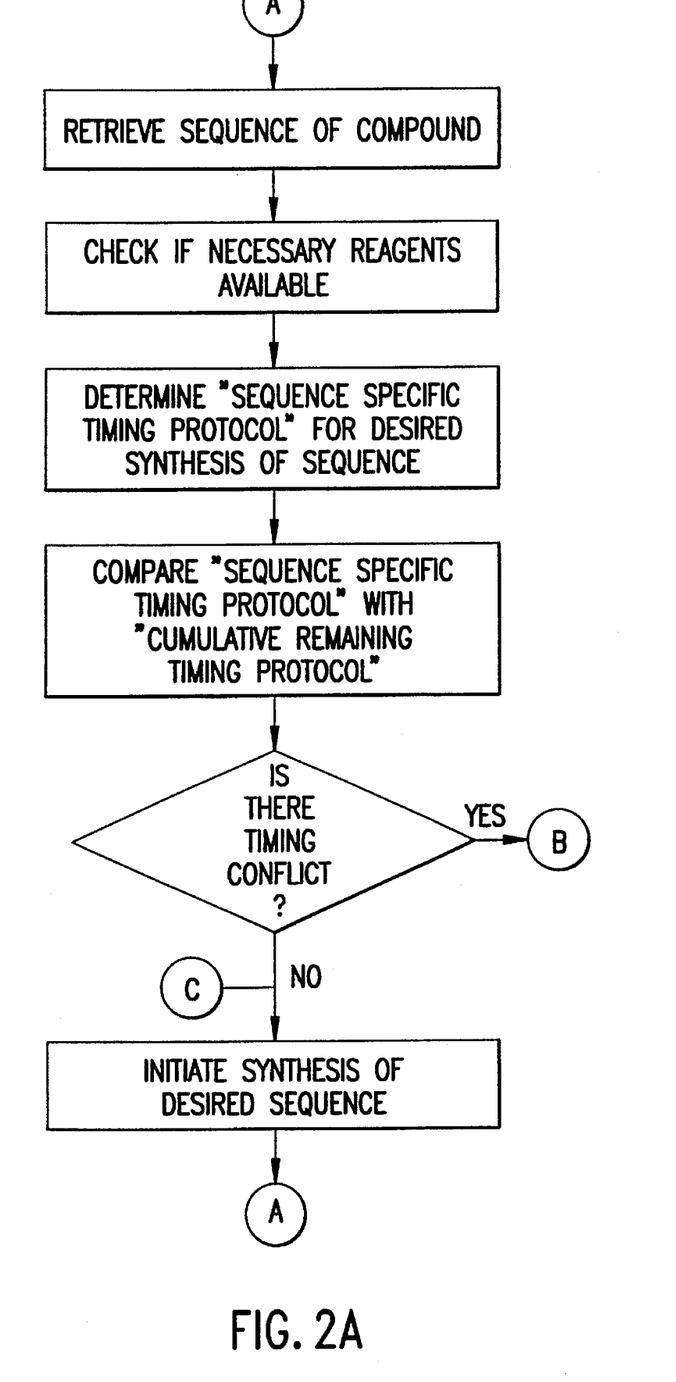
FIGS. 2A and 2B are illustrative flow charts representing the operation of the synthesis system of FIG. 1, and more particularly, the timing protocol.
Figure 2B:
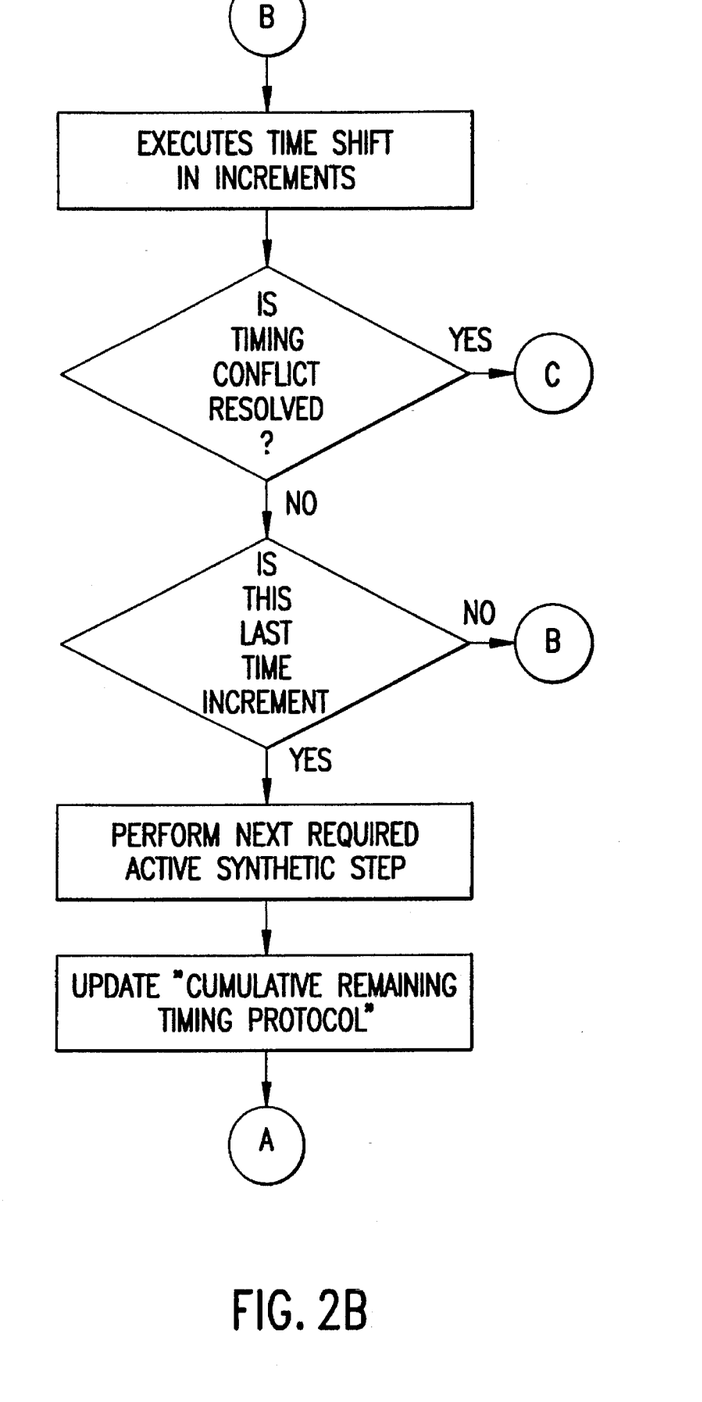

In order to better understand the timing protocol that allows the handling of multiple synthetic tasks more efficiently, a discussion of the underlying basis for the timing protocol would be instructive, particularly with reference to the flow charts of FIGS. 2A and 2B.

To begin with, the user enters the sequence of compounds to be synthesized. And, if the necessary reagents are available, the system will start to initiate a desired synthesis—otherwise, the user is notified of the deficiencies. More particularly, for each desired synthesis, the system determines the particular synthetic steps, both active and passive, that are required to synthesize the sequence as well as determines when those synthetic steps are to be performed—that is, their timing or temporal relationship within the synthetic cycle.

Those skilled in the art will readily note that these synthetic steps are sequence specific, that is they are specifically correlated to the desired synthesis. Herein, these synthesis steps are referred to as a "sequence specific timing protocol." In considering to initiate a new synthesis, the "sequence specific timing protocol" of the new desired synthesis is compared to the sequence specific steps or timing protocol for those sequences already initiated. These latter sequence specific steps are referred to as a "cumulative remaining timing protocol" because they are a compilation of all the individual "sequence specific timing protocols" of currently initiated syntheses.

More particularly, the above comparison requires the system to plot out when the active synthetic steps of the new desired synthesis occur with respect to the active synthetic steps of the sequences currently being synthesized. And, unless there is a timing conflict in performing the active synthetic steps of the new desired synthesis and those already initiated, the system begins to initiate the start of the new synthesis, if necessary reagents are available. It should be understood that the new sequence specific timing protocol of the desired new synthesis is added to the "cumulative remaining timing protocol."

Should, however, a timing conflict exist, the system attempts to determine if the initiation of the new desired synthesis can be delayed or "time shifted", up and until the start of the next active synthetic step of any of the initiated syntheses, so as to eliminate the timing conflict. Unless the system is able to resolve the timing conflict, the system will not initiate the new desired synthesis, but will instead proceed to execute the next required active synthetic step of the syntheses currently in progress. Once the active synthetic step has been performed, the system updates the "cumulative remaining timing protocol" and then attempts again to resolve the timing conflict during the next passive synthetic step of any of the ongoing syntheses. This timing protocol is repeatably performed until all the desired syntheses have been initiated.

Below is an illustrative description of the synthetic steps for the simultaneous synthesis of multiple peptides in accordance with the principles of the timing protocol discussed above. It should be recalled that each synthetic protocol in the multiple synthesis is a sequenced cycle order of preprogrammed steps or procedures. For this illustrative description, one synthetic cycle consists of the following synthetic steps: (i) washing the resin three times with dimethylformamide (DMF) for thirty (30) seconds each time; (ii) deprotecting the amino acid with fifty percent (50%) solution of piperidine/DMF for ten (10) minutes; (iii) washing the resin five (5) times with dimethylformamide (DMF) for thirty (30) seconds each time; and (iv) two (2) hour coupling using three (3) molar excess of DIC/HOBt activated Fmoc protected amino acids.

After finishing the last synthetic cycle for each peptide, the synthesis is finished by washing, or by washing, deprotecting and washing, if that is applicable.

Robot system 30 operating in accordance with the above illustrative synthetic cycle positions a first resin syringe (peptide synthesis no. 1), manipulates the plunger to aspirate a wash solution of dimethylformamide (DMF), and then shakes the resin syringe. This washes the resin with wash solution for thirty (30) seconds. Preferably, the washing is repeated three times. Subsequently, the first resin syringe is used to aspirate from the delivery cup the deprotection reagents that have been dispensed by the piston pump. This latter step is the "adding deprotection reagents" step. This repeated washing and adding deprotection reagents takes about five (5) minutes.

During deprotection, which lasts about ten (10) minutes, the synthesis system can advantageously direct the robot system to initiate washing and adding deprotection reagents for a second resin syringe or the next peptide synthesis (peptide synthesis no. 2). Since that washing and adding deprotection reagents, however, only takes less than five minutes, there are at least five minutes still remaining before the deprotection is completed for the first resin syringe. To ensure that the respite time between steps is minimized, the synthesis system further directs the robot system to initiate yet another washing and adding deprotection reagents for a third resin syringe (peptide synthesis no. 3).

Determining whether to initiate another washing and adding deprotection reagents for a subsequent resin syringe (the next peptide synthesis) is controlled automatically under program control by comparing the sequence specific timing protocol with the cumulative remaining timing protocol, as discussed above. In effect, washing and adding deprotection agents are initiated if the least remaining time for deprotection is sufficiently long to complete the task.

Once deprotection has been completed for the first resin syringe, the synthesis system directs the robot system to position the first resin syringe so as to wash the resin for thirty seconds with dimethylformamide (DMF). This is repeated, preferably, five times, after which the resin syringe is positioned in a temporary holding location. The amino acid syringe containing the desired amino acid to be coupled is next positioned and a preprogrammed amount dispensed into the delivery cup which then receives a DIC solution. The first resin syringe is used to aspirate from the delivery cup the amino acid solution so as to couple that amino acid. This latter step is the "adding coupling reagents" step. Likewise, the time for washing and adding coupling reagents takes about five (5) minutes. During that coupling, the synthesis system advantageously directs the robot system to initiate coupling for the second resin syringe (peptide synthesis no. 2), and then subsequently for the third resin syringe (peptide synthesis no. 3).

Similarly, determining whether to initiate another washing and add coupling reagents for a subsequent resin syringe or peptide synthesis is controlled automatically under program control by comparing the sequence specific timing protocol with the cumulative remaining timing protocol, as discussed above. In effect, washing and adding coupling reagents are initiated if the least remaining time for coupling is sufficiently long to complete the task.

Once coupling has been initialized for all three resin syringes, that is the three peptide syntheses, the synthesis system takes a fourth resin syringe (peptide synthesis no. 4) and initiates washing and deprotection. The synthesis system initiates washing and deprotection for as many resin syringes (peptide syntheses) as possible before the least remaining coupling time expires.

This procedure is repeated until the sequence of the shortest length peptide is assembled. If desired, an additional resin syringe can then be used to synthesize a new peptide sequence.

The maximum amount of peptide synthesized is limited by the size of the syringe. For example, with 10 ml syringes containing about 500 mg of resin (0.5 mmol/g resin), it is anticipated that 0.25 mmol of peptide (ca 300 mg crude decapeptide) can be synthesized.

Those skilled in the art will readily note in the above illustrative description that the coupling time for each peptide synthesis is the same—the earliest initiated coupling finishing prior to subsequently initiated couplings. In that situation, each new initiated synthetic cycle for a peptide synthesis follows the order in which the prior cycle was initiated. Of course, it should be understood that different coupling times, if that is desired, may be used. The principles of the timing protocol, however, do not change—the system, if time permits, initiates an active synthesis step of the next peptide synthesis during the passive steps of the prior peptide synthesis.

A program listing implementing the principles of the invention, including the timing protocol, is contained in the microfiche appendix.

Figure 3:
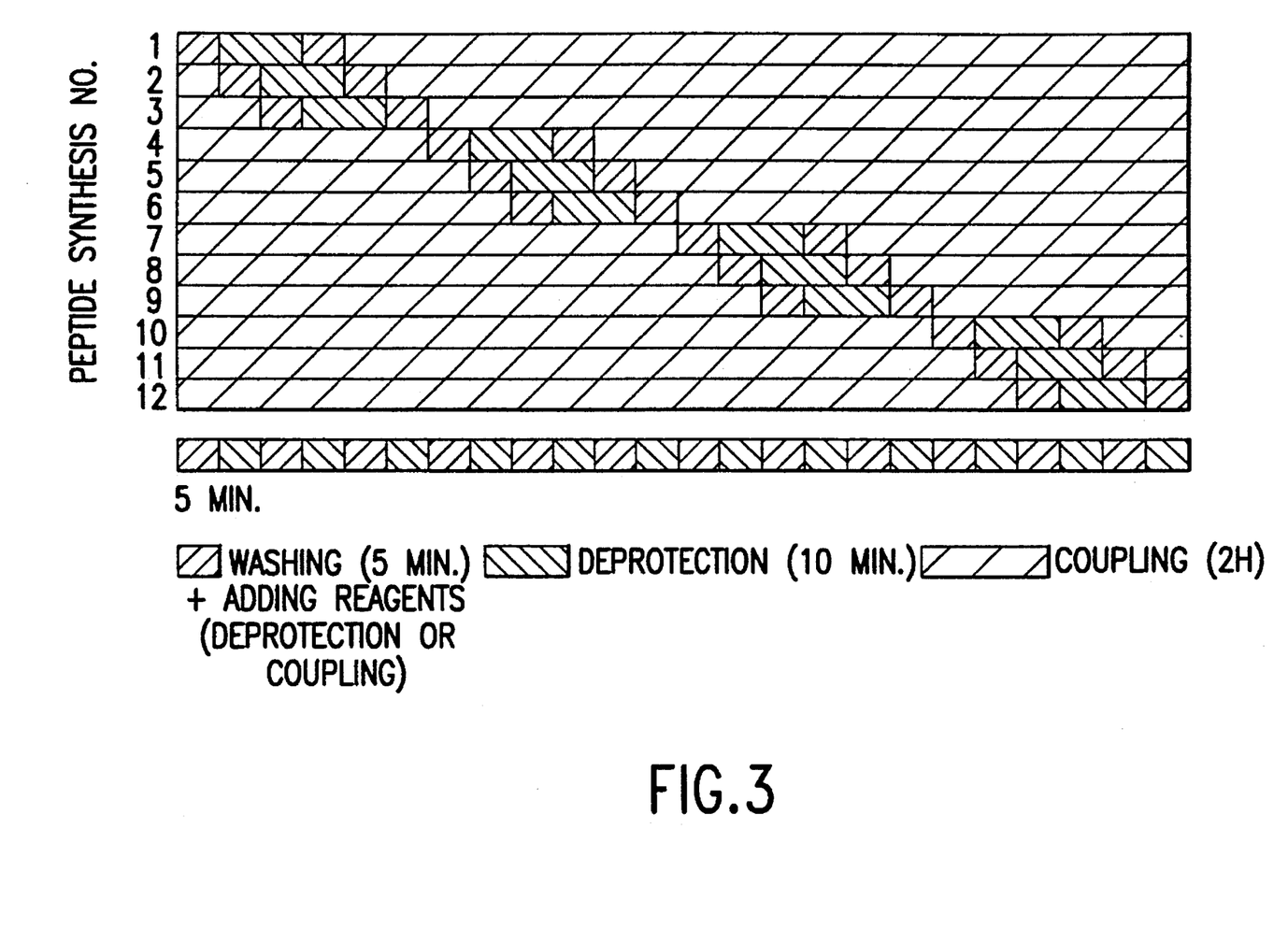
FIG. 3 is a chart illustrative of the timing protocol for the synthesis system of FIG. 1.

Referring to FIG. 3, there is illustrated the timing protocol or timing relationship between washing, adding deprotection reagents, deprotection, adding coupling reagents and coupling for the multiple synthesis of twelve peptides using the above described solid phase peptide synthetic protocol. Those skilled in the art will readily note based on the discussion above that during passive synthetic steps (deprotection and coupling), active synthetic steps in the synthetic cycles of the next peptide synthesis are concurrently initiated with the prior peptide synthesis. For example, referring to FIG. 3, during deprotection of the first peptide synthesis (peptide synthesis no. 1), washing and adding deprotection reagents is initiated for the second and third peptide syntheses (peptide synthesis nos. 2 and 3).

It should be understood that prior to initiating the synthesis of each compound, various parameter variables must be specified, in the synthetic protocol of each desired peptide synthesis, including the kind and amount of solvent or reagents to be dispensed, and the length of time of the corresponding washing steps and/or reaction steps. Also, because aspiration is performed in adding deprotection reagents and adding coupling reagents, the volume of air necessary to enable the efficient mixing of the resin and solvent must be specified.

In addition to the various parameter variables which must be specified or retrieved from existing stored synthetic protocols, the synthesis system must also be initialized with other information, including the assignment and identification of solvents and reagents contained in the peptide synthetic protocols; the reagent and amino acid concentrations (mmol/ml) used to calculate the corresponding reagent and amino acid solution volumes, respectively; the size of the syringes; the amount of resin in the syringes; the substitution of resin in mmol/g; the positions and content of each amino acid syringe, preferably identified by a three to five letter code, including its concentration and available volume; the peptide sequences desired to be synthesized using the identifying three to five letter codes; and for each peptide its identifying code, and sequence. Preferably, the system prompts the user for the information. Alternatively, however, this information may be entered prior to initiating the peptide syntheses or stored in a file or database.

The order in which sequences to be synthesized are entered establishes their priority for synthesis, and establishes a synthesis queue. Advantageously, any compound can be entered with any priority. Also, additional sequences can be added to the synthesis queue together with the necessary synthetic protocol. Also, additional reagents may be added, if necessary.

From the above information, the system calculates whether the amount of amino acid and reagents is sufficient to prepare all the peptides. Unless there is enough amino acid and reagents available for the synthesis, the synthesis system will not initiate that synthesis, indicating instead its status as "not ready." Significantly, the above timing protocol allows handling multiple synthetic tasks efficiently since active synthetic steps requiring the use of the robot system in the synthesis cycles of multiple peptides are performed concurrently with passive synthetic steps in different synthetic cycles. Moreover, because synthesis resources become immediately available with each completed synthesis, a new peptide synthesis can be initiated without waiting for the complete synthesis of the entire set of desired peptides. Preferably, the new peptide synthesis is taken from the top of a waiting list of peptides that has been prioritized according to need. Advantageously, that prioritized waiting list can be changed at any time, either by adding or deleting any peptide, to meet varying situations. Further, any peptide currently being synthesized can be halted without affecting the synthesis of the others.

Advantageously, since there is neither a physical link between the reagent vessels and the reaction vessels nor between the mixing chambers and the reaction vessels, different reagents and reaction conditions may be used within the same or different peptide synthesis. Such flexibility, of course, allows for the synthesis of libraries requiring variable numbers of building block reagents.

To test the reliability and throughput of the above novel peptide synthesis system, five different peptide amides (Ile Lys Arg Lys Arg, SEQ ID NO:1; Val Arg Tyr Gly Ile, SEQ ID NO:2; Ala Ala Ala Gly Tyr, SEQ ID NO:3; Phe Pro Arg Gly Arg, SEQ ID NO:4; Val Tyr Phe Ala Trp, SEQ ID NO:5) were synthesized using a RAM TentaGel resin in accordance with the principles of the invention. (See the attached Sequence Listing). Also, a mixture K (82.5% trifluoroacetic acid, 5% pcresol, 5% thioanisole, 2.5% ethanedithiol and 5% water) was used to deprotect side chains and to cleave the peptides from the resin. Results from that experimental practice indicate, a high degree of purity of the crude material based on analytical gradient HPLC traces and molecular peak analysis using mass spectroscopy.

It is understood that various other modifications will also be readily apparent to those skilled in the art without departing from the scope and spirit of the invention. For example, the principles of the invention can be equally applied to any chemistry that involves repeated procedures, such as washing, deprotection and coupling—particularly, solid phase synthesis, including but not limited to the organic reactions described in Borchardt et al., *J. Am. Chem. Soc.*, 116: 373 (1994); Chen et al., *J. Am. Chem. Soc.*, 116: 2661 (1994); Simon et al., *PNAS*, 89: 9367 (1992); Nikolaiev et al., *Pept. Res.*, 6: 161–70 (1993); and Lebl et al., Vol. 5: 541–548, *Techniques In Protein Chemistry*, Academic Press, San Diego (1994).

Accordingly, it is not intended that the scope of the claims appended hereto be limited to the description set forth herein, but rather that the claims be construed as encompassing all the features of the patentable novelty that reside in the present invention, including all features that would be treated as equivalents thereof by those skilled in the art to which this invention pertains.

We claim:

1. A system for the solid phase synthesis of multiple species of organic compounds each formed by repeated synthetic cycles of synthetic steps, said system comprising:

a computer for processing a program of instructions correlated to predetermined synthetic cycles for the synthesis of each of said multiple species;

an automated robot responsive to said computer, said automated robot operative to cause said synthetic steps to be performed in accordance with the synthetic cycles of each of said multiple species; and a timing protocol, implemented by said program of instructions and executed by said computer, for directing synthetic steps of at least two different species to be performed concurrently, said timing protocol determining if the time for a synthetic step in the synthetic cycle of one of said at least two different species is sufficient for initiating a synthetic step in the synthetic cycle of another of said at least two different species.

2. The system of claim 1 wherein each of said species has an associated sequence specific timing protocol, the compilation of all sequence specific timing protocols of species currently under synthesis being a cumulative remaining timing protocol, said system further including means for determining whether there is a timing conflict between the sequence specific timing protocol of a new desired species and the cumulative remaining timing protocol.

3. The system of claim 1 wherein said synthetic steps include the steps of washing, adding deprotection reagents, deprotection, adding coupling reagents and coupling.

4. The system of claim 1 wherein said synthetic steps include active and passive synthetic steps, said timing protocol directing said active steps within a first synthesis of a first species to be performed concurrently with passive steps within a second synthesis of a second species.

5. The system of claim 1 wherein said organic compounds include peptides.

6. The system of claim 1 further comprising:

a first set of a plurality of syringes, each syringe containing resin for repeatably coupling compounds to a solid support so as to synthesize a first species; and a second set of a plurality of syringes, each syringe containing a desired compound that is to be coupled to the solid support during one of said synthetic cycles.

7. The system of claim 6 where said compound that is to be coupled is an amino acid for the synthesis of a peptide.

8. The system of claim 7 wherein said solid phase synthesis is a Merrifield solid phase peptide synthesis.

9. The system of claim 6 wherein said automated robot includes a gripper arm responsive to said computer, said gripper arm selectively positioning and manipulating syringes from said first and second sets of a plurality of syringes to thereby aspirate or dispense solvents and reagents required within said synthetic cycles.

10. The system of claim 1 further comprising a database containing parameter variables required for the synthesis of said multiple species of organic compounds, said database including the characteristic sequence of the repeated synthetic cycles for each of said multiple species.

11. A system for the solid phase synthesis of multiple peptides each formed by repeated synthetic cycles of synthetic steps, said system comprising:

a first set of syringes each holding a solid support;

a second set of syringes each holding a desired amino acid, said first set of syringes serving as the reaction vessels for coupling desired amino acids from said second set of syringes to the solid supports;

a computer for processing a program of instructions correlated to predetermined synthetic cycles for the synthesis of multiple peptides; and an automated robot responsive to said computer, said automated robot operatively coupled to said first and second sets of syringes for aspirating and dispensing reagents so as to cause said repeated synthetic cycles to be performed in accordance with a desired peptide synthesis to thereby repeatably couple a desired amino acid to a solid support, said repeated [synthesis]synthetic cycles including the synthetic steps of washing, adding deprotection reagents, deprotection, adding coupling reagents and coupling, said repeated synthetic cycles performed in accordance with a timing protocol wherein said washing, adding deprotection reagents or adding coupling reagents is performed concurrently with said deprotection or coupling for different peptide syntheses.

12. The system of claim 11 wherein said first set of syringes is made of polypropylene.

13. The system of claim 11 wherein each of said first set of syringes includes a solid phase retaining device.

14. The system of claim 13 wherein said solid phase retaining device is a frit.

15. The system of claim 11 wherein said solid support comprises a resin selected from the group consisting of polystyrene and polyethylene glycol.

16. The system of claim 11 where said automated robot includes an arm operatively connected to said robot so as to manipulate each of said first and second sets of syringes.

17. The system of claim 16 wherein said first and second sets of syringes each includes a plunger operatively coupled thereto, said plunger movable by said arm of said automated robot to thereby aspirate or dispense reagents.

18. The system of claim 17 wherein the content amount of reagents in each of said syringes is determined by the plunger position of the corresponding syringe.

19. The system of claim 11 further including an optical sensor responsive to the movement of said first and second sets of syringes, said optical sensor confirming the positioning of said first and second sets of syringes.

20. The system of claim 11 wherein said synthesis of peptides employs Fmoc/tBu chemistry.

21. The system of claim 11 further comprising piston pumps and delivery cups, said piston pumps delivering solvents and reagents to said delivery cups from which said first and second sets of syringes dispense or aspirate said solvents or reagents.

22. The system of claim 11 further including a database containing parameter variables required for the synthesis of the multiple peptides.

23. A process for the solid phase automated synthesis of multiple species of organic compounds formed by repeated synthetic cycles of synthetic steps, said process comprising the steps of:

a) initiating a synthetic step in a synthetic cycle of a species;

b) determining if the time for said synthetic step of step a) is sufficient for initiating a synthetic step in the synthetic cycle of a different species, and if so, c) initiating a synthetic step in the synthetic cycle of said different species; and d) repeating steps a), b) and c) until said multiple species are synthesized.

24. The process of claim 23 wherein said synthetic steps include washing, deprotection and coupling for the synthesis of multiple peptides.

25. The process of claim 24 wherein said deprotection and coupling are performed in a plurality of syringes which serve as reaction vessels.

26. A process for the automated solid phase synthesis of multiple peptides formed by repeated cycles of washing, adding deprotection reagents, deprotection, adding coupling reagents and coupling so as to repeatably couple amino acids to a solid support, said process comprising the steps of:

a) filling a first set of syringes, each with a resin solid support;

b) filling a second set of syringes, each with a desired amino acid;

d) washing one of said first set of syringes with a first solution;

e) adding deprotection solution to the syringe of step d) to initiate deprotection;

f) while deprotection of step e) is proceeding repeating steps d) and e) if the time for performing those steps is less than the time required for deprotection, otherwise proceeding with step g);

g) adding coupling solution to the syringe of step d) to initiate coupling to thereby couple a desired amino acid to the solid support; and h) while coupling of step g) is proceeding repeating steps f) and g) if the time for performing those steps is less than the time for coupling, otherwise proceeding with steps d) and e) until the time for coupling expires.

27. The process of claim 26 wherein steps a) through h) are repeated until a peptide is synthesized.

28. The process of claim 26 further comprising the step of washing each of said first set of syringes of step d) prior to adding coupling solution.

29. The process of claim 26 wherein the system is automated through the use of a robot, said robot adding coupling and deprotection solution by manipulating the syringes so as to aspirate and dispense reagents.

30. The process of claim 26 wherein the first solution is dimethylformamide.

31. The process of claim 26 wherein the deprotection solution is piperidine/DMF.

32. The process of claim 26 wherein the coupling solution is a solution of DIC/HOBt.

33. The process of claim 26 further comprising the step of interactively prompting a user for parameter variables thereby forming a database required for the synthesis of the multiple peptides, said database including the characteristic amino acid sequence of each of the multiple peptides.

34. The process of claim 26 further comprising the step of adding or deleting peptide sequences to a list of peptides to be synthesized.

35. A process for the solid phase automated synthesis of multiple species of organic compounds formed by repeated synthetic cycles of synthetic steps, said process comprising the steps of:

a) determining a sequence specific timing protocol associated with a desired species to be synthesized, said sequence specific timing protocol including when each synthetic step for the desired species occurs temporally;

b) determining the cumulative remaining timing protocol of species currently under synthesis, said cumulative remaining timing protocol including when each synthetic step for the species currently under synthesis occurs temporally; and c) determining whether a timing conflict exists between said sequence specific timing protocol and said cumulative remaining timing protocol, a timing conflict occurring when one synthetic step for the desired species to be synthesized cannot be performed concurrently with the synthetic steps of species currently under synthesis.

36. The process of claim 35 further comprising the step of time shifting the synthesis initiation of the desired species to be synthesized so as to resolve the time conflict.

37. The process of claim 35 wherein a time conflict occurs when an active synthetic step of the desired species to be synthesized is temporally coincident with any active synthetic steps for the species currently under synthesis.

38. The process of claim 35 wherein said organic compounds includes peptides.

39. The process of claim 35 further comprising the step of entering parameter variables required for the synthesis of the organic compounds.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:

(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:1:

Ile Lys Arg Lys Arg
1               5

(2) INFORMATION FOR SEQ ID NO:2:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:2:

Val Arg Tyr Gly Ile
1               5

(2) INFORMATION FOR SEQ ID NO:3:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:3:

Ala Ala Ala Gly Tyr
1               5

(2) INFORMATION FOR SEQ ID NO:4:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:4:

Phe Pro Arg Gly Arg
1               5

(2) INFORMATION FOR SEQ ID NO:5:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:5:

Val Tyr Phe Ala Trp
1               5